United States Patent
Suh et al.

(10) Patent No.: US 7,205,394 B2
(45) Date of Patent: Apr. 17, 2007

(54) CLATHRATE OF AZITHROMYCIN HYDRATE WITH 1,2-PROPYLENEGLYCOL, METHOD FOR THE MANUFACTURE THEREOF AND PHARMACEUTICAL COMPOSITION COMPRISING SAME

(75) Inventors: Kwee-Hyun Suh, Icheon-si (KR); Gi-Jeong Kim, Seoul (KR); Sang-Min Yoon, Seongnam-si (KR); Mi-Ra Seong, Seongnam-si (KR); Gwan-Sun Lee, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 10/476,016

(22) PCT Filed: Apr. 25, 2002

(86) PCT No.: PCT/KR02/00761

§ 371 (c)(1),
(2), (4) Date: Oct. 23, 2003

(87) PCT Pub. No.: WO02/085898

PCT Pub. Date: Oct. 31, 2002

(65) Prior Publication Data

US 2004/0132673 A1    Jul. 8, 2004

(30) Foreign Application Priority Data

Apr. 25, 2001    (KR) ................................ 2001-22406

(51) Int. Cl.
*C07H 1/00* (2006.01)
*C07H 17/08* (2006.01)
(52) U.S. Cl. .................................... 536/7.4; 536/18.5
(58) Field of Classification Search ................ 536/7.4, 536/18.5; 514/29
See application file for complete search history.

(56) References Cited

U.S. PATENT DOCUMENTS 6,586,576 B2 *   7/2003   Aronhime et al. ........... 536/7.4
6,977,243 B2 *  12/2005   Li et al. ......................  514/29

FOREIGN PATENT DOCUMENTS

| EP | 0 984 020 A2 | 3/2000 |
| WO | WO 00/02567 | 1/2000 |
| WO | WO 02/07736 A1 | 1/2002 |

* cited by examiner

*Primary Examiner*—Elli Peselev
(74) *Attorney, Agent, or Firm*—Anderson Kill & Olick, PC

(57) ABSTRACT

A clathrate of azithromycin hydrate with 1,2-propyleneglycol is much less hygroscopic than azithromycin hydrate or crystals known in the art, therefore, it can be useful for the preparation of a medicine for treating various microbial infections.

6 Claims, 7 Drawing Sheets

CLATHRATE OF AZITHROMYCIN HYDRATE WITH 1,2-PROPYLENEGLYCOL, METHOD FOR THE MANUFACTURE THEREOF AND PHARMACEUTICAL COMPOSITION COMPRISING SAME

FIELD OF THE INVENTION

This invention relates to a novel clathrate of azithromycin hydrate with 1,2-propyleneglycol, a process for its manufacture, and a pharmaceutical composition containing the clathrate.

BACKGROUND OF THE INVENTION

Azithromycin, 9-deoxo-9a-aza-9a-methyl-9a-homoerythromycin A (N-methyl-11-aza-10-deoxo-10-dehydroerythromycin A: IUPAC) of formula (II) disclosed in U.S. Pat. Nos. 4,517,358 and 4,474,768, is an azalide-type semi-synthetic macrolide antibiotic, useful for treating bronchial infection, sexual contact infection and dermatological infection (See Kirste and Sides; *Antimicrob. Agents Chemother.*, 33, 1419 (1989)).

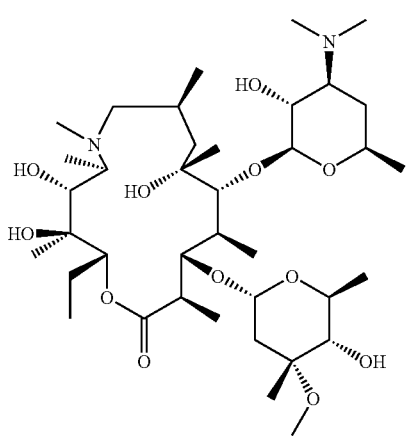

(II)

Azithromycin is known to exist in three forms, the anhydride, monohydrate and dihydrate forms. These forms have been identified by powder X-ray diffraction and differential scanning calorimetric studies.

Azithromycin anhydride, which is disclosed in U.S. Pat. No. 4,517,359, is non-crystalline product and thus, its highly hygroscopic property is not suitable for pharmaceutical formulation.

Further, azithromycin monohydrate (mp. 136° C.), as described in U.S. Pat. No. 4,474,768 and WO Publication No. 89/00576, is crystalline but it has also hygroscopic property, making it difficult to maintain its water content at a constant level.

WO Publication No. 89/00576 discloses a process for preparing azithromycin dihydrate (mp. 126° C.) from azithromycin monohydrate by recrystallizing from a mixture of tetrahydrofuran, water and a $C_5 \sim C_7$ aliphatic hydrocarbon. Although the dihydrate is less hydroscopic than the monohydrate, the water content thereof must be carefully maintained during a vaccum drying step at a relatively low temperature. Such a water content controlling procedure is, however, not sufficient for removing the toxic aliphatic hydrocarbon solvent rigorously used in the recrystallization procedure. On the other hand, vacuum drying in higher temperature may result in formation of azithromycin dihydrate having undesirable water content.

Accordingly, many attempts have been made to develop a novel crystal or solvate form of azithromycin. For example, EP Publication No. 0,984,020 discloses a clathrate of azithromycin monohydrate with isopropanol of formula (III).

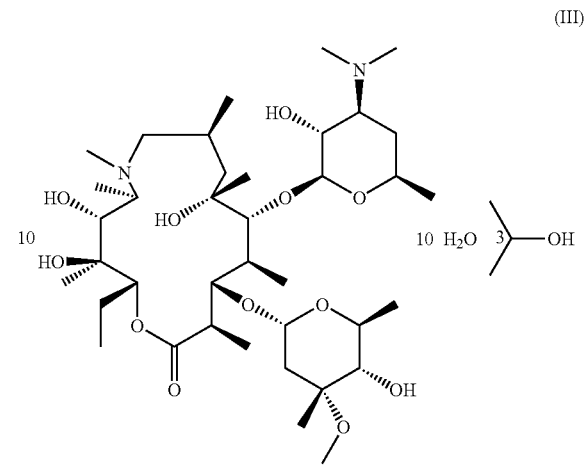

(III)

WO Publication No. 00/32203 discloses an ethanol solvate of azithromycin hydrate of formula (IV).

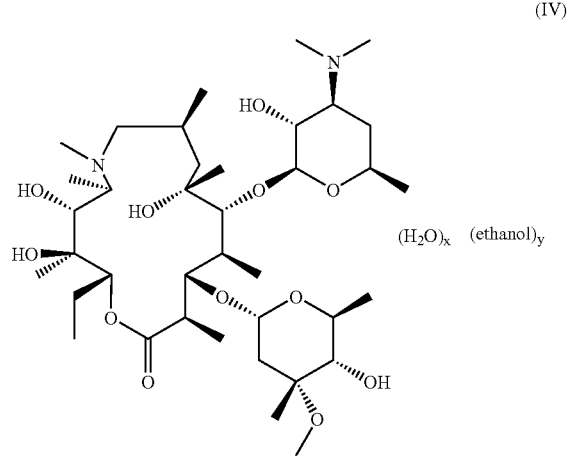

(IV)

However, there has existed a need to develop an improved crystal form of azithromycin crystal suitable for pharmaceutical applications.

SUMMARY OF THE INVENTION

It is, therefore, an object of the present invention to provide a novel form of azithromycin, which can be useful for the preparation of a medicine for treating various microbial infections.

In accordance with the present invention, there is provided a novel clathrate of azithromycin hydrate with 1,2-propyleneglycol of formula (I):

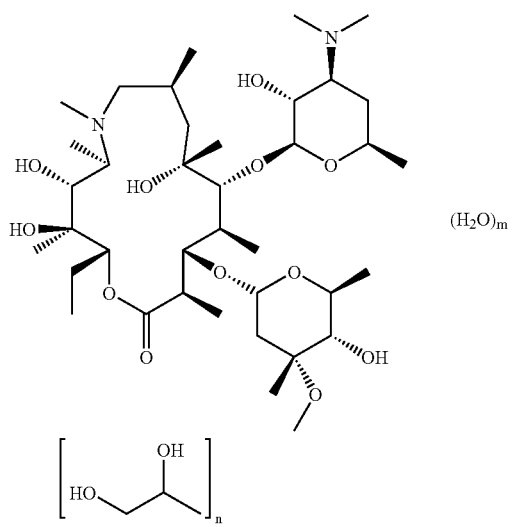

wherein m ranges from 1 to 2 and n, from 0.20 to 0.40.

The present invention further provides a process for preparing the clathrate of formula (I), comprising the steps of: (1) dissolving azithromycin in acetone then adding 1,2-propyleneglycol and water thereto to obtain a crystalline product; and (2) filtering the crystals formed, washing the crystals with water and drying to produce the azithromycin clathrate crystals.

The present invention also provides a pharmaceutical composition for treating microbial infection, comprising the clathrate of formula (I) and a pharmaceutically acceptable carrier.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The compound of formula (I) may be prepared by (1) dissolving azithromycin in a suitable amount of acetone, preferably 2 to 10 ml of acetone per g of azithromycin, adding 1,2-propyleneglycol thereto in an amount of 0.25 to 2.5 nm based on 1 ml of acetone while maintaining at a temperature ranging from room temperature (R.T.) to the boiling point of acetone, adding water in an amount of 1 to 3 ml per ml of acetone, stirring the mixture for 30 minutes to 4 hours at a, temperature ranging from 0° C. to room temperature, filtering precipitated crystals, washing the crystals with water and drying for 12 to 24 hours at a temperature ranging from 40° C. to 45° C.

The 1,2-propyleneglycol moiety of the inventive clathrate is essentially non-toxic ($LD_{50}$: 25 ml/kg, at oral administration in rat), and it can exist in the form of a racemate, an S-isomer, or an R-isomer.

The azithromycin being used in the preparation of the inventive clathrate may be anhydride, monohydrate, dihydrate, isopropanol clathrate, or ethanol solvate of azithromycin known in the art or a mixture thereof, and it can be prepared by any of the methods disclosed in U.S. Pat. Nos. 4,517,359 and 4,474,768 and Korean Patent Application No. 2001-14659.

Figure 4:
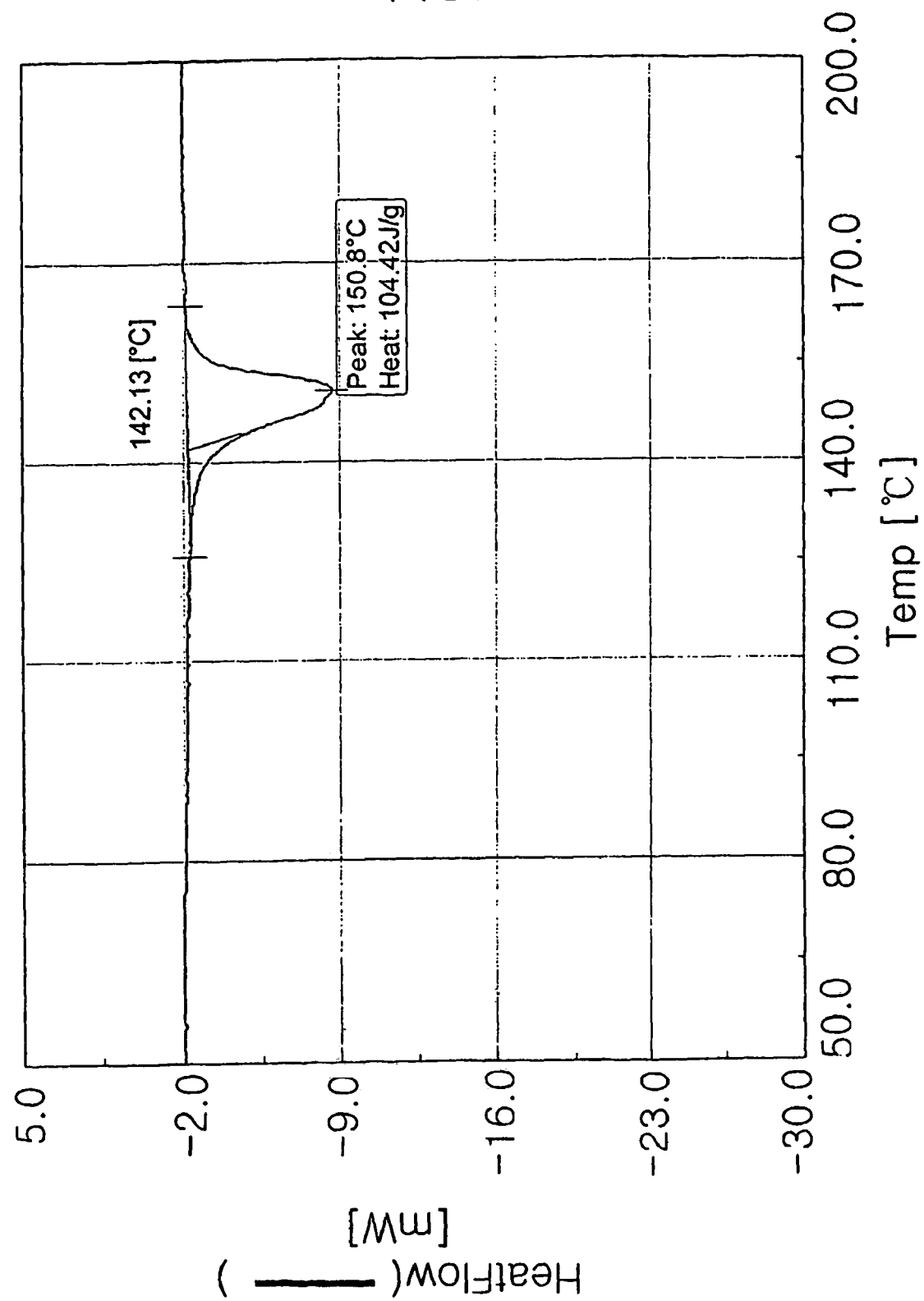
FIG. 4: a differential scanning calorimetric scan of the compound of the present invention.
Figure 5:
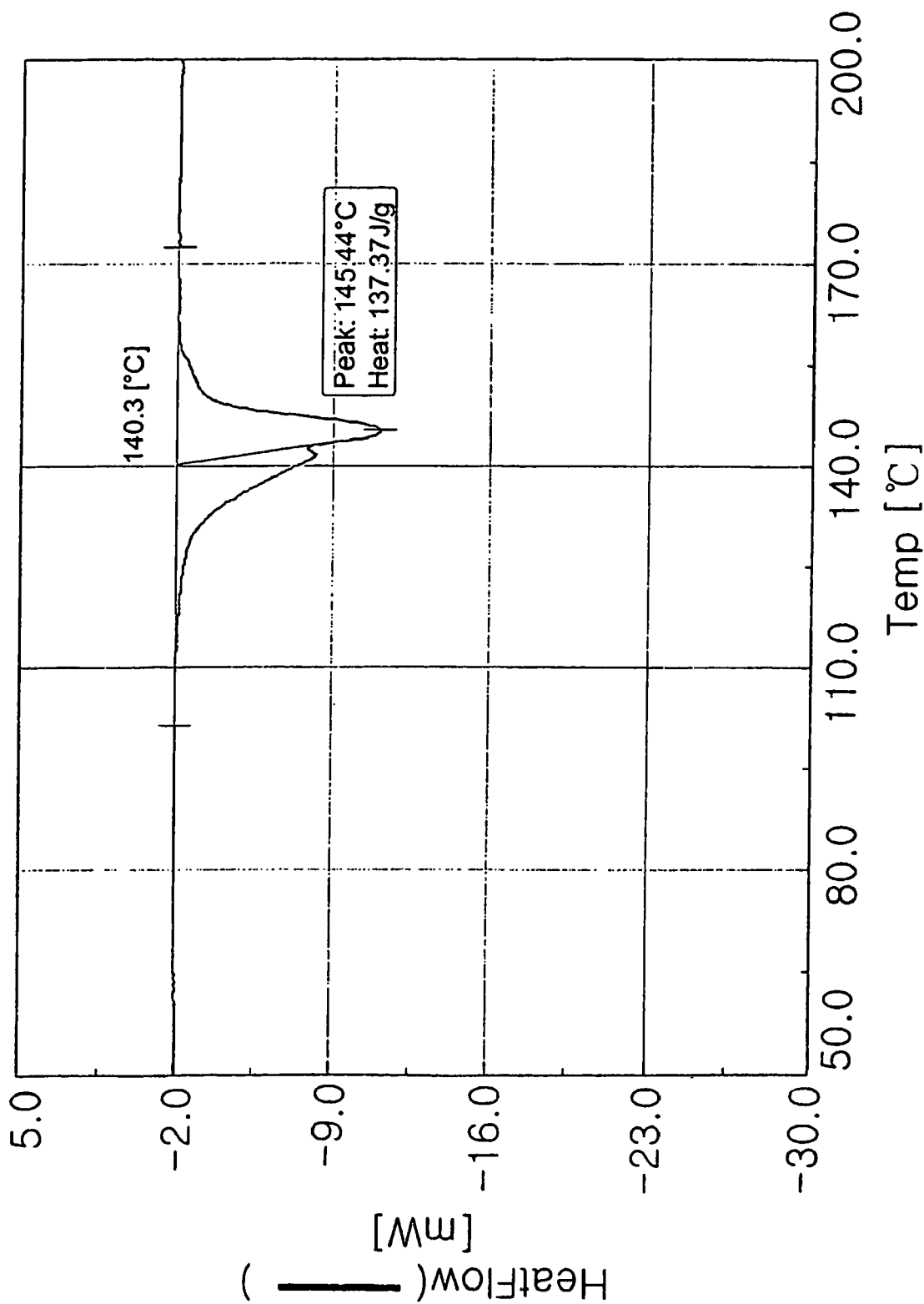
FIG. 5: a differential scanning calorimetric scan of azithromycin monohydrate.

The novel clathrate compound of the present invention melts approximately at 130° C., shows in a DSC scan an endothermic peak at 150.8° C. and heat capacity of 104.42 J/g, as shown in FIG. 4. These thermal properties are completely different from those of the monohydrate form (endothermic peak 145.44° C.; heat capacity: 137.37 J/g) or the dihydrate form (endothermic peak 142.72° C.; heat capacity: 160.15 J/g), shown in FIG. 5 and FIG. 6, respectively.

Figure 2:
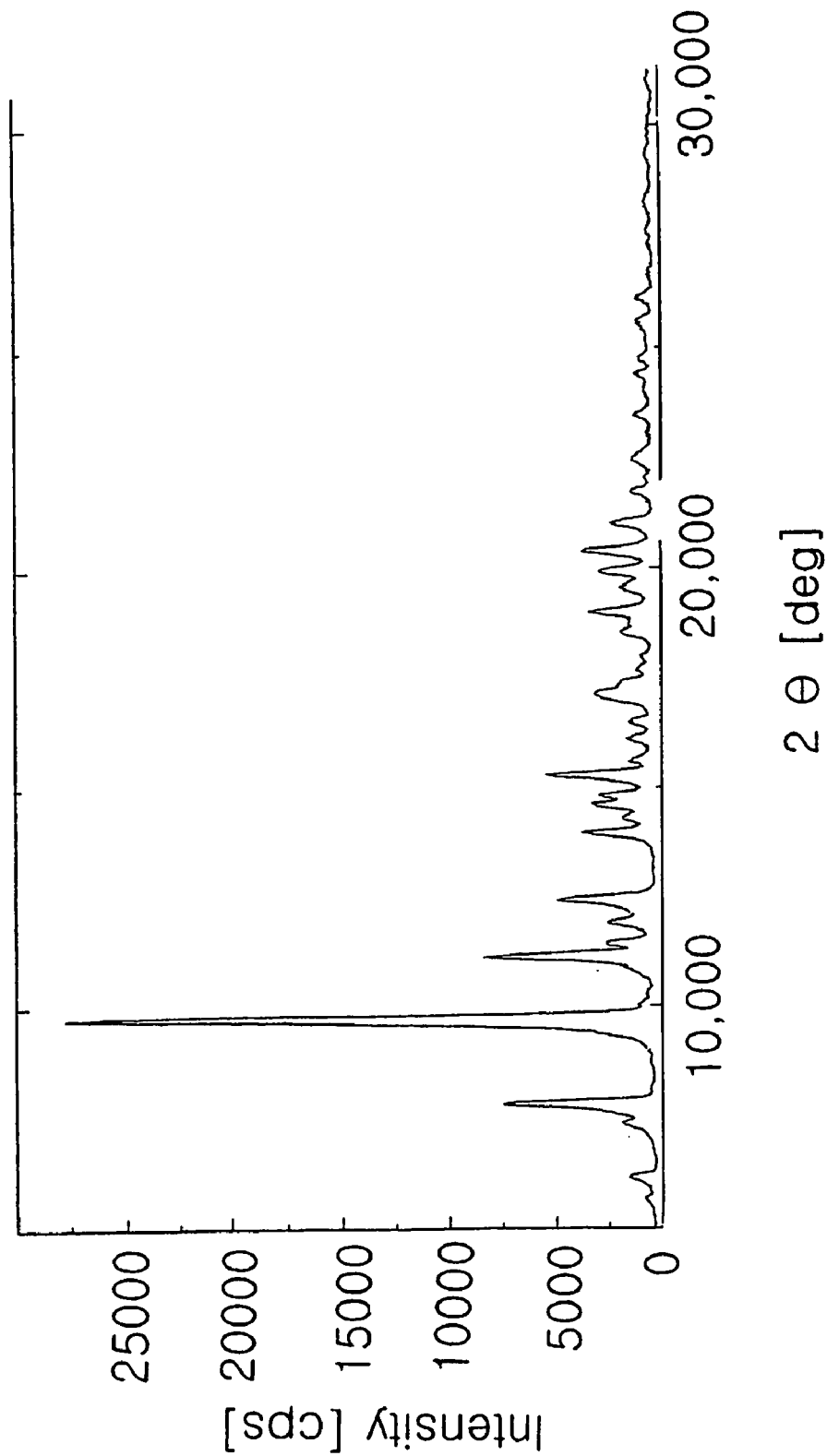
FIG. 2: a powder X-ray diffraction spectrum of azithromycin monohydrate.
Figure 3:
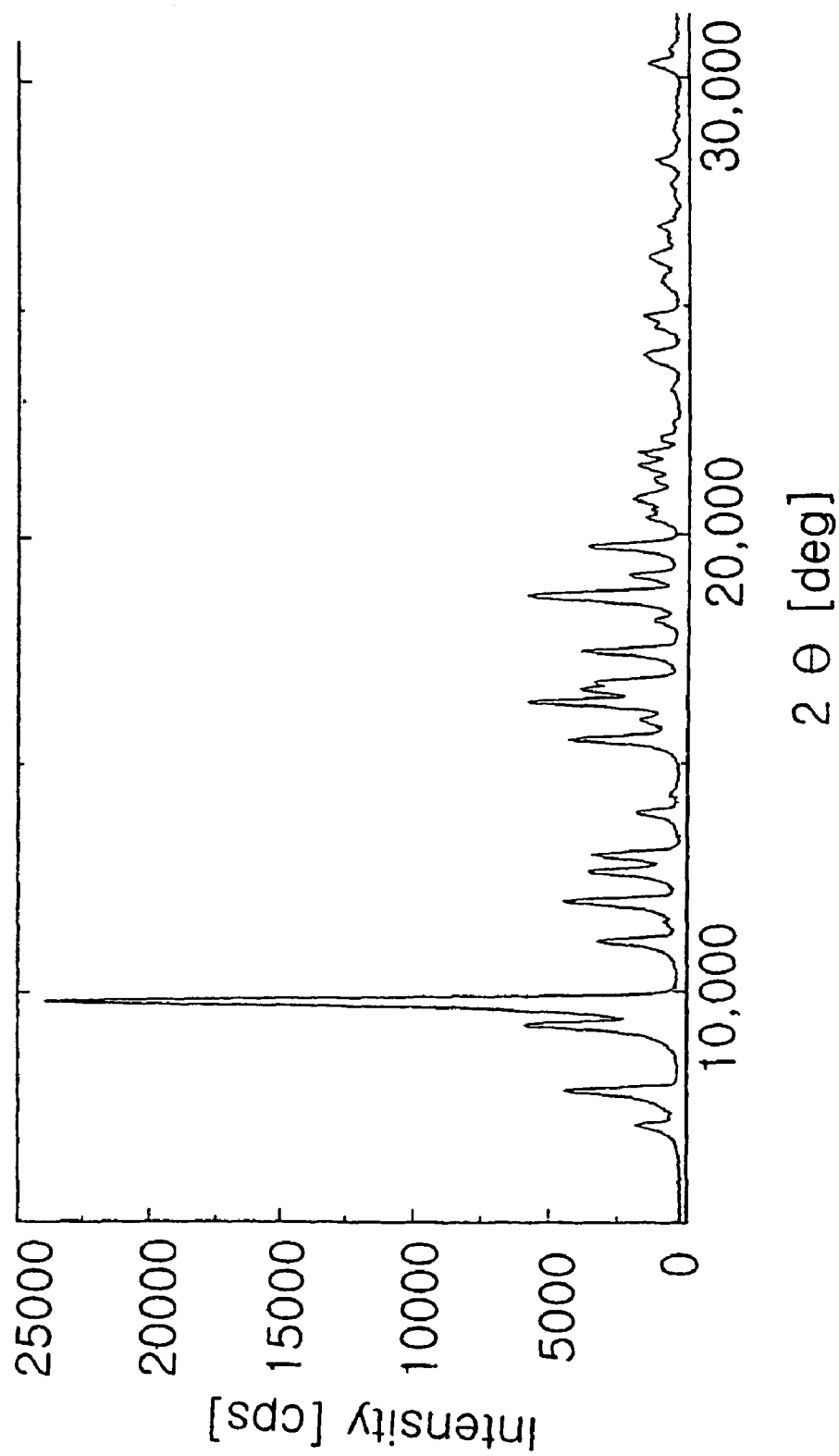
FIG. 3: a powder X-ray diffraction spectrum of azithromycin dihydrate.

The crystal structure of the clathrate compound of the present invention differs from those of the monohydrate and dihydrate form, as the powder X-ray diffraction patterns shown in FIG. 4, FIG. 2 and FIG. 3, respectively.

The water content of the inventive clathrate determined by a Karl-Fischer water analyzer ranges from 2.3 to 4.6%, preferably, from 3.0 to 4.0%, more preferably, from 3.1 to 3.7%, while its 1,2-propyleneglycol content determined with a gas chromatography or $^1$H-NMR spectroscopy ranges from 2.1 to 4.1%, preferably, from 2.4 to 3.8%.

The inventive clathrate of formula (I) preferably has an m value of 1.5±0.2 and an n value of 0.30±0.06.

The clathrate compound of the present invention is much less hygroscopic than azithromycin anhydride or azithromycin monohydrate, and its water content remains more or less constant when stored under a humid condition, unlike azithromycin dihydrate.

The clathrate compound of present invention can be used in formulating various pharmaceutical compositions for treating various microbial infection. Such a composition contains the inventive clathrate together with pharmaceutically acceptable excipients and carriers, which may be administrated orally, injectably, rectally, transdermally, bucally or nasally. Suitable forms for oral administration include tablets, compressed or coated pills, dragees, sachets of powder for reconstitution, hard or soft gelatin capsules, syrups and emulsions et al. Suitable forms for parenteral administration include aqueous or non-aqueous solution, emulsion, while for rectal administration suitable forms include suppositories with hydrophilic or hydrophobic vehicles. For topical application the invention provides ointments or aerosol formulations known in the art; for transdermal delivery, there are provided suitable delivery systems as known in the art. For nasal delivery there are provided suitable aerosol delivery systems known in the art.

This invention will be better understood from the Examples that follow. However, the examples illustrate, but do not limit, the invention. Those skilled in the art will readily appreciate that the specific methods and results discussed are merely illustrative of the invention as described more fully in the claims that follow thereafter.

EXAMPLE 1

100 g of azithromycin anhydride was dissolved in 300 ml of acetone and 100 ml of 1,2-propylene glycol was added thereto. The solution was stirred for 10 minutes at R.T. and 500 mg of water was added dropwise thereto to induce the precipitation of azithromycin crystals. The solution was stirred for 2 hours at R.T. and the precipitate was filtered, washed rigorously with water, and then dried at 40° C. for 20 hours to give 96 g of a clathrate of azithromycin hydrate with 1,2-propyleneglycol.

m. p: 129 to 131° C.,

The water content determined by a Karl Fischer water analyzer: 3.5 wt %, The 1,2-propyleneglycol content determined with a gas chromatography: 3.3 wt %.

EXAMPLE 2

20 g of azithromycin monohydrate was dissolved in 100 ml of acetone and 15 ml of 1,2-propylene glycol was added thereto. The solution was stirred for 10 minutes at R.T. and 200 ml of water was added dropwise thereto to induce the precipitation of azithromycin crystals. The solution was stirred for 2 hours at 0 to 5° C. and the precipitate was filtered, washed rigorously with water, and then dried at 40° C. for 20 hours to give 18.2 g of a clathrate of azithromycin hydrate with 1,2-propyleneglycol.

m. p: 130 to 132° C.,

The water content: 3.4 wt %,

The amount of 1,2-propyleneglycol: 3.2 wt %.

EXAMPLE 3

20 g of azithromycin monohydrate was dissolved in 120 mb of acetone and 15 mg of 1,2-propylene glycol was added thereto. The solution was stirred for 10 minutes at R.T. and 180 ml of water was added dropwise thereto to induce the precipitation of azithromycin crystals. The solution was stirred for 3 hours at 0 to 5° C. and the precipitate was filtered, washed rigorously with water, and then dried at 40° C. for 20 hours to give 17.6 g of a clathrate of azithromycin hydrate with 1,2-propyleneglycol.

m. p: 130 to 132° C.,

The water content: 3.4 wt %, The 1,2-propyleneglycol content: 3.5 wt %.

TEST EXAMPLE 1

Figure 6:
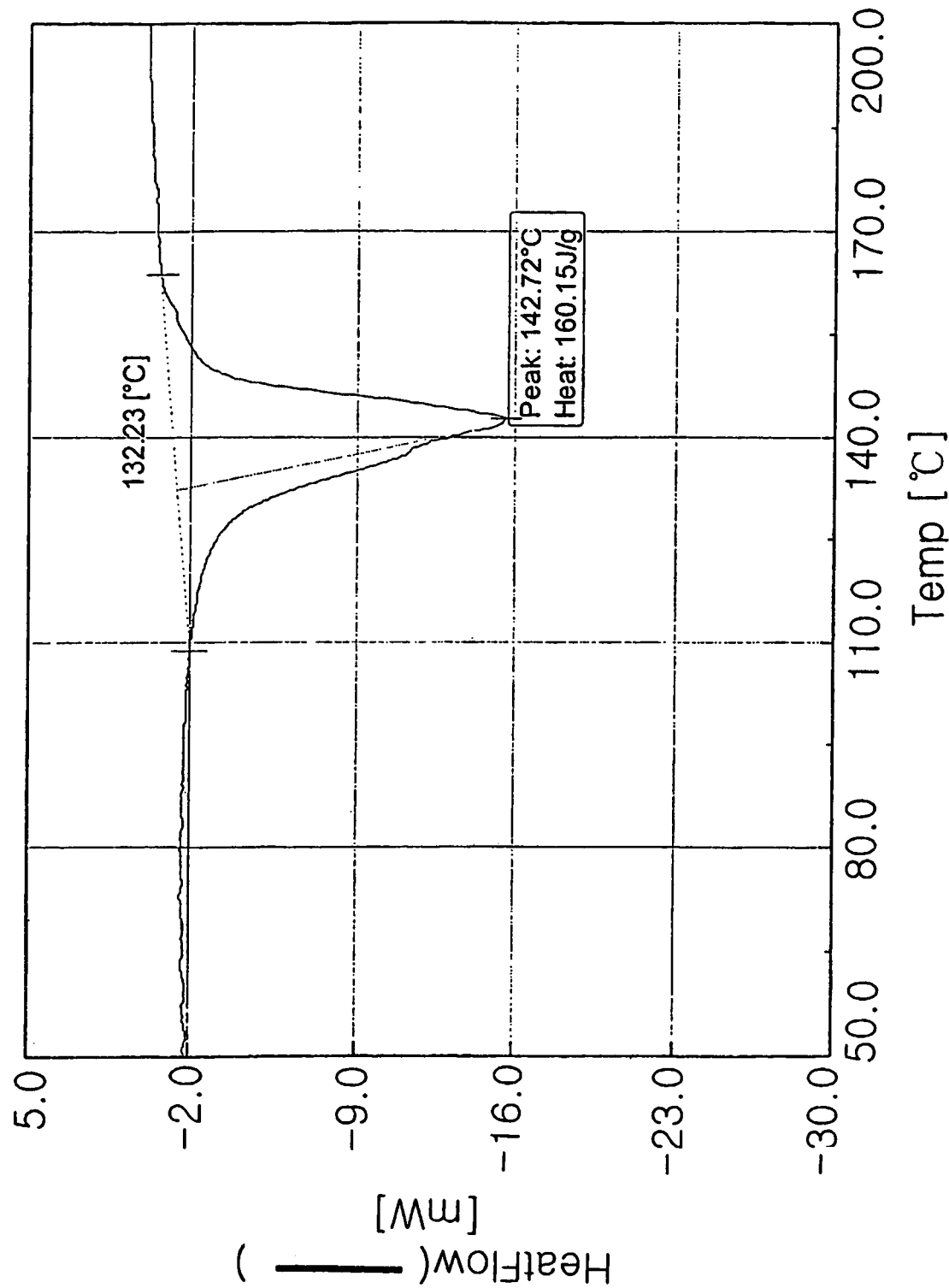
FIG. 6: a differential scanning calorimetric scan of azithromycin dihydrate.

The compound obtained in Example 1, azithromycin monohydrate and dihydrate obtained by the methods in accordance with U.S. Pat. No. 5,869,629 were subjected to differential scanning calorimetric measurements (heat speed 10° C./minutes.). The inventive compound of Example 1 showed an endothermic peak at 150.8° C. and heat capacity of 104.42 J/g, as shown in FIG. 4. The azithraycin monohydrate, on thee other hand, showed an endothermic peak at 145.44° C. and heat capacity of 137.37 μg (FIG. 5), while azithromycin dihydrate, an endothermic peak at 142.72° C. and heat capacity of 160.15 J/g (FIG. 6).

Figure 1:
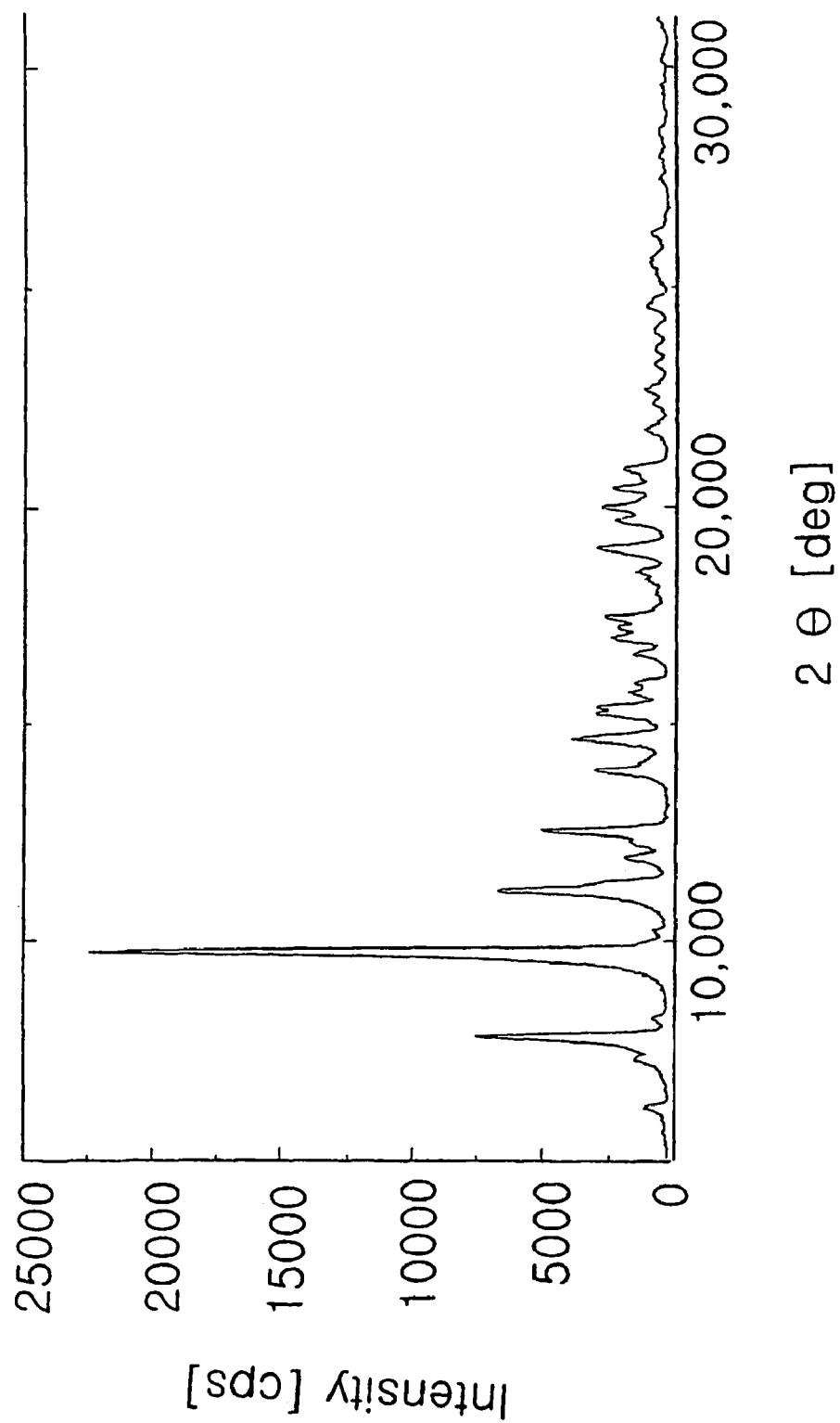
FIG. 1: a powder X-ray diffraction spectrum of the compound of the present invention.

Further, the X-ray diffraction spectra of above three compounds are illustrated in FIG. 1, FIG. 2 and FIG. 3, respectively. The X-ray results summarized in Table 1 show that the compound of present invention has a crystal structure which is completely different from those of the known compounds.

Figure 7:
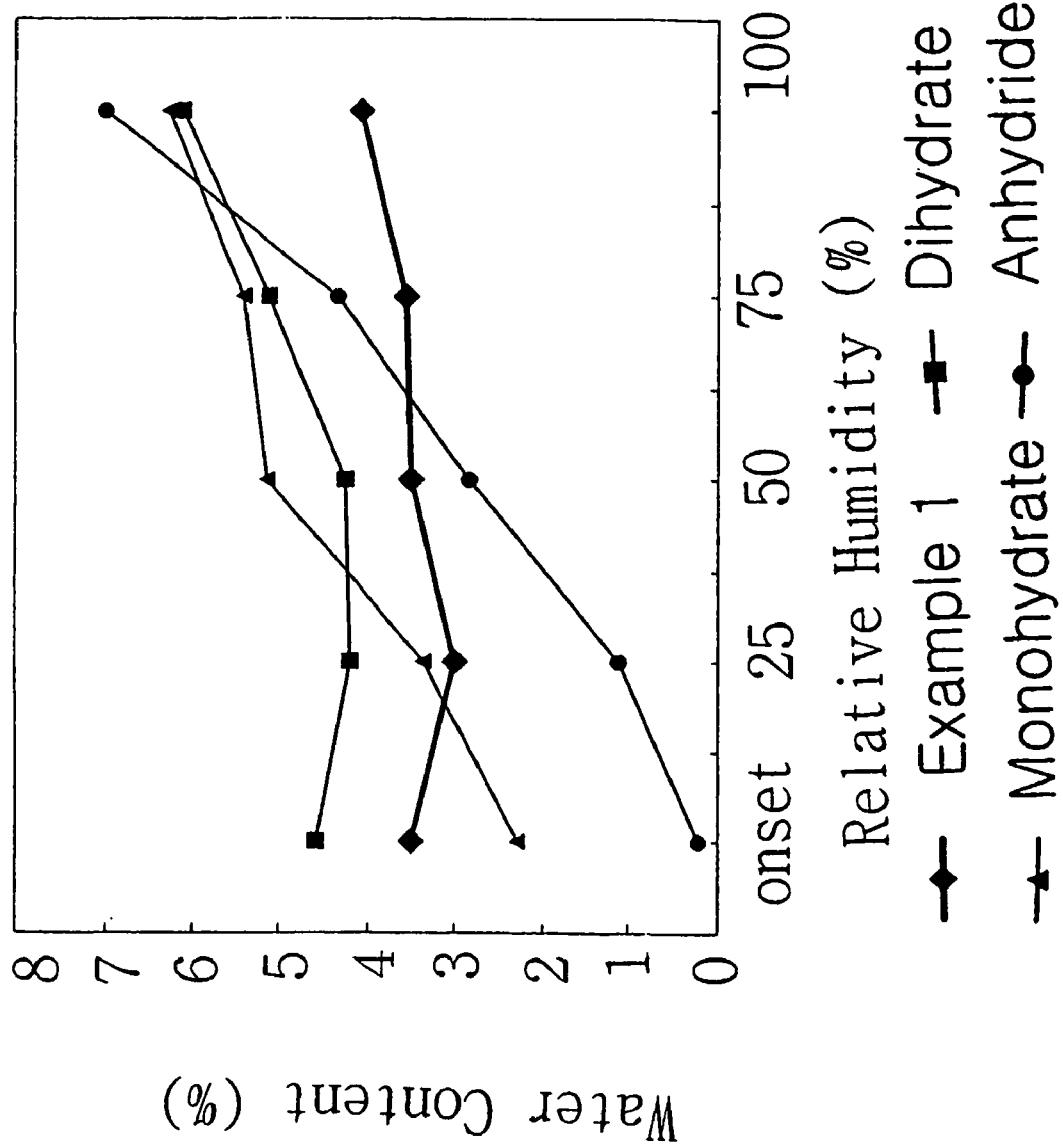
FIG. 7: comparative hygroscopic properties of the compound of the present invention, azithromycin anhydride, monohydrate, and dihydrate.

Also, the hygroscopic properties of each of the compound obtained in Example 1 (1), azithromycin dihydrate (2), monohydrate (3), and anhydride (4) were determined by exposing each sample to a relative humidity of each 25%, 50%, 75% or 100% for 7 days and measuring the water content thereof by the Karl Fischer method. The result is shown in Table 2 and FIG. 7.

TABLE 1

| Radiation: Cu K-α1 | Operation: 40 kV/126 mA |
| Divergence slit: 1° | Scan Mode: continuous |
| Scattering slit: 1° | Scan speed: 5°/min |
| Receiving slit: 0.15 mm | Scan step: 0.02° |

| 2 theta(°2Θ) | d-value(A) | I/Io(≧2) |
| --- | --- | --- |
| 6.200 | 14.2437 | 3 |
| 7.300 | 12.0996 | 5 |
| 7.820 | 11.2962 | 32 |
| 8.220 | 10.7474 | 2 |
| 9.740 | 9.0733 | 100 |
| 10.220 | 8.6482 | 2 |
| 11.140 | 7.9360 | 29 |
| 11.900 | 7.4308 | 7 |
| 12.220 | 7.2369 | 6 |
| 12.500 | 7.0754 | 22 |
| 13.880 | 6.3749 | 12 |
| 14.640 | 6.0456 | 16 |
| 15.220 | 5.8165 | 12 |
| 15.400 | 5.7490 | 12 |
| 15.700 | 5.6398 | 6 |
| 15.940 | 5.5554 | 6 |
| 16.620 | 5.3296 | 6 |
| 16.960 | 5.2235 | 10 |
| 17.220 | 5.1452 | 9 |
| 17.460 | 5.0750 | 11 |
| 18.060 | 4.9078 | 2 |
| 18.300 | 4.8439 | 3 |
| 18.500 | 4.7920 | 5 |
| 19.040 | 4.6573 | 12 |
| 19.660 | 4.5118 | 9 |
| 19.980 | 4.4403 | 12 |
| 20.400 | 4.3498 | 10 |
| 20.860 | 4.2549 | 8 |
| 21.740 | 4.0846 | 4 |
| 22.320 | 3.9798 | 3 |
| 22.640 | 3.9242 | 5 |
| 23.220 | 3.8275 | 2 |
| 23.540 | 3.7762 | 3 |
| 23.960 | 3.7109 | 3 |
| 24.520 | 3.6274 | 4 |
| 24.720 | 3.5985 | 3 |
| 25.260 | 3.5228 | 2 |
| 25.500 | 3.4902 | 3 |
| 26.200 | 3.3985 | 4 |
| 28.440 | 3.1357 | 2 |
| 31.080 | 2.8751 | 2 |
| 33.600 | 2.6650 | 2 |

TABLE 2

| | (1) | (2) | (3) | (4) |
| --- | --- | --- | --- | --- |
| Onset | 3.50 | 4.58(4.1) | 2.30(3.2) | 0.22 |
| Relative humidity 100% | 4.06 | 6.11(5.2) | 6.29(7.2) | 7.00 |
| Relative humidity 75% | 3.55 | 5.10(4.6) | 5.41(6.6) | 4.33 |
| Relative humidity 50% | 3.50 | 4.25(4.6) | 5.13(5.6) | 2.85 |
| Relative humidity 25% (33%) | 3.01 | 4.20(2.5) | 3.35(2.3) | 1.11 |
| Calculated water content (%) | 3.38[1)] | 4.60 | 2.35 | 0.00 |

TABLE 2-continued

|  | (1) | (2) | (3) | (4) |
|---|---|---|---|---|
| Found-Calculated (Difference, %) | −0.37~+0.68 | −0.4~+1.51 (−2.1~+0.6) | +1~+3.94 (−0.05~+4.84) | +1.11~+7.00 |
| Range of Difference (%) | 1.05 | 1.91(2.7) | 3.94(4.9) | 7.00 |

Note:
[1])Calculated based on m = 1.5 and n = 0.30 in formula (I).
2) The numbers in parenthesis are values obtained after 3 days at the corresponding relative humidity.

Table 2 clearly shows that the novel clathrate compound of the present invention is much less hygroscopic than other compounds.

While the embodiments of the subject invention have been described and illustrated, it is obvious that various changes and modifications can be made therein without departing from the spirit of the present, invention which should be limited only by the scope of the appended claims.

What is claimed is:

1. A clathrate compound of azithromycin hydrate with 1,2-propyleneglycol of formula (I):

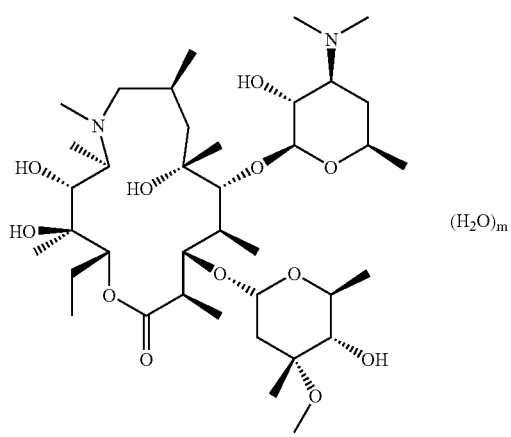

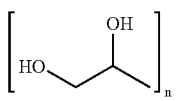

wherein m ranges from 1 to 2 and n, from 0.20 to 0.40.

2. The compound of claim 1, wherein water content ranges from 2.3 to 4.6% and 1,2-propyleneglycol content is between 2.1 and 4.1%.

3. A process for preparing the azithromycin clathrate compound of formula (I) of claim 1, comprising the steps of: (1) dissolving azithromycin in acetone and adding 1,2-propyleneglycol and water thereto to obtain a crystalline product; and (2) filtering the crystals formed, washing the crystals with water and drying to produce the azithromycin clathrate crystals.

4. The process of claim 3, wherein 2 to 10 ml of acetone is employed per g of azithromycin.

5. The process of claim 3, wherein 0.25 to 2.5 ml of 1,2-propyleneglycol is used per ml of acetone.

6. The process of claim 3, wherein 1 to 3 ml of water is used per me of acetone.

* * * * *